(12) United States Patent
Ho et al.

(10) Patent No.: US 8,813,745 B2
(45) Date of Patent: Aug. 26, 2014

(54) RESISTANCE MATCHING IN A PATIENT CIRCUIT

(75) Inventors: Peter Chi Fai Ho, Pittsburgh, PA (US); Zachary Dean Paul, Pittsburgh, PA (US)

(73) Assignee: Koninklijke Philips N.V., Eindhoven (NL)

( * ) Notice: Subject to any disclaimer, the term of this patent is extended or adjusted under 35 U.S.C. 154(b) by 519 days.

(21) Appl. No.: 13/131,613

(22) PCT Filed: Nov. 21, 2009

(86) PCT No.: PCT/IB2009/055246
§ 371 (c)(1),
(2), (4) Date: May 27, 2011

(87) PCT Pub. No.: WO2010/067234
PCT Pub. Date: Jun. 17, 2010

(65) Prior Publication Data
US 2011/0226246 A1    Sep. 22, 2011

Related U.S. Application Data

(60) Provisional application No. 61/121,589, filed on Dec. 11, 2008.

(51) Int. Cl.
*A61M 11/00*    (2006.01)

(52) U.S. Cl.
USPC ............. 128/204.18; 128/204.21; 128/204.22

(58) Field of Classification Search
CPC .................... A61M 16/06; A61M 2016/0027; A61M 16/00; A61M 2016/0039
USPC ........................................ 128/204.18–204.23
See application file for complete search history.

(56) References Cited

U.S. PATENT DOCUMENTS

| 4,448,192 | A | 5/1984 | Stawitcke | |
|---|---|---|---|---|
| 6,158,432 | A * | 12/2000 | Biondi et al. | 128/204.21 |
| 6,837,242 | B2 * | 1/2005 | Younes | 128/204.22 |
| 8,020,555 | B2 * | 9/2011 | Rapoport | 128/204.21 |
| 2002/0014239 | A1 | 2/2002 | Chalvignac | |
| 2004/0094157 | A1 | 5/2004 | Dantanarayana | |
| 2007/0044798 | A1 | 3/2007 | Levi | |

FOREIGN PATENT DOCUMENTS

| JP | 2001009035 | | 1/2001 |
|---|---|---|---|
| JP | 2007531540 | A | 11/2007 |
| JP | 2008264566 | | 6/2008 |
| JP | 2008531136 | A | 8/2008 |
| WO | WO2006024532 | A1 | 3/2006 |

* cited by examiner

*Primary Examiner* — Steven Douglas
(74) *Attorney, Agent, or Firm* — Michael W. Haas

(57) ABSTRACT

A system configured to deliver pressurized gas to an airway of a subject in accordance with a predetermined therapeutic algorithm. The system includes a pressure generator that generates a pressurized flow of breathable gas and a circuit that communicates the pressurized flow of breathable gas from the pressure generator to the airway of the subject. In order to facilitate the delivery of the pressurized gas to the airway of the subject in accordance with the predetermined therapeutic algorithm, a resistance of the circuit to gas flow is supplemented so that the overall resistance of the circuit is at or near a predetermined level.

15 Claims, 8 Drawing Sheets

RESISTANCE MATCHING IN A PATIENT CIRCUIT

CROSS-REFERENCE TO RELATED APPLICATIONS

This patent application claims the priority benefit under 35 U.S.C. §119(e) of U.S. Provisional Application No. 61/121,589 filed on Dec. 11, 2008, the contents of which are herein incorporated by reference.

BACKGROUND OF THE INVENTION

1. Field of the Invention

The invention relates to supplementing the resistance to gas flow in a circuit configured to deliver gas to a subject in order to bring the overall resistance of the circuit to a predetermined level that corresponds to an assumed level of resistance accounted for an a therapeutic algorithm.

2. Description of the Related Art

Systems that deliver pressurized flows of breathable gas to subjects are known. In these systems, a circuit generally carries the gas from a pressure generator to the airway of a subject. These circuits can be configured in accordance with individual preferences of the subject. For example, the interface appliance (e.g., the mask), the circuit length, the physical flexibility of the circuit, and/or other features of the circuit can be configured by the subject. Generally, different circuit configurations will have different resistances to gas flow.

Generally, a system delivers a pressurized flow of breathable gas to a subject in accordance with a predetermined therapeutic algorithm. The algorithm dictates one or more of the parameters of the gas (e.g., pressure, flow rate, composition, temperature, humidity, etc.) delivered to the subject over time. Since some of the parameters of the gas provided to the subject vary within the circuit between the pressure generator and the airway of the subject due to the resistance within the circuit, some conventional systems account for the resistance within the circuit. Typically, this involves controlling the pressure generator to adjust the parameters of the gas as it is emitted by the pressure generator to account for the resistance of the circuit.

SUMMARY OF THE INVENTION

One aspect of the invention relates to a circuit that defines a gas flow path between a pressure generator and an airway of a subject to enable the provision of gas from the pressure generator to the airway of the subject. In one embodiment, the circuit comprises an interface appliance, a conduit, and one or more flow limiting features. The interface appliance is configured to provide gas to and receive gas from an airway of a subject, with the interface appliance forming a flow path between a conduit interface opening and one or more subject interface openings. The one or more subject interface openings communicate gas between the airway of the subject and the interior of the interface appliance, and the flow path formed by the interface appliance between the conduit interface opening and the one or more subject interface openings has a first resistance to gas flow. The conduit forms a flow path between a first opening and a second opening, wherein the first opening receives gas from a pressure generator, wherein gas within the flow path formed by the conduit is communicated to the conduit interface opening of the interface appliance via the second opening, and wherein the flow path formed by the conduit between the first opening and the second opening has a second resistance to gas flow. The one or more flow limiting features are disposed within the circuit, and provide a supplemental resistance to gas flow within the circuit. The overall resistance to gas flow within the circuit is a function, at least in part, of an aggregation of the first resistance, the second resistance, and the supplemental resistance, and the one or more flow limiting features are configured such that the supplemental resistance increases the overall resistance to gas flow within the circuit to a predetermined resistance.

Another aspect of the invention relates to a method of providing a circuit that defines a gas flow path between a pressure generator and an airway of a subject to enable the provision of gas from the pressure generator to the airway of the subject. In one embodiment, the method comprises configuring a circuit that forms a flow path for delivering gas from a pressure generator to an airway of the subject, with the circuit comprising an interface appliance and a conduit. The interface appliance is configured to provide gas to and receive gas from an airway of a subject, and forms a flow path between a conduit interface opening and one or more subject interface openings. The one or more subject interface openings communicate gas between the airway of the subject and the interior of the interface appliance, and the flow path formed by the interface appliance between the conduit interface opening and the one or more subject interface openings has a first resistance to gas flow. The conduit forms a flow path between a first opening and a second opening, wherein the first opening receives gas from a pressure generator, wherein gas within the flow path formed by the conduit is communicated to the conduit interface opening of the interface appliance via the second opening, and wherein the flow path formed by the conduit between the first opening and the second opening has a second resistance to gas flow. The method may further comprise supplementing the overall resistance of the circuit to gas flow so that the overall resistance of the circuit to gas flow reaches a predetermined resistance, wherein supplementing the overall resistance of the circuit comprises including within the circuit one or more flow limiting features, the one or more flow limiting features providing a supplemental resistance to gas flow within the circuit that increases the overall resistance of the circuit to the predetermined resistance.

Another aspect of the invention relates to a circuit that defines a gas flow path between a pressure generator and an airway of a subject to enable the provision of gas from the pressure generator to the airway of the subject. In one embodiment, the circuit comprises means for interfacing the circuit with the airway of a subject to provide gas to and receive gas from the airway of the subject, wherein the means for interfacing has a first resistance to gas flow; means for conveying gas between a pressure generator and the means for interfacing, wherein the means for conveying gas has a second resistance to gas flow; means for limiting gas flow within the circuit, the means for limiting gas flow providing a supplemental resistance to gas flow within the circuit; wherein the overall resistance to gas flow within the circuit is a function, at least in part, of an aggregation of the first resistance, the second resistance, and the supplemental resistance, and wherein the means for limiting gas flow are configured such that the supplemental resistance increases the overall resistance to gas flow within the circuit to a predetermined resistance.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

DETAILED DESCRIPTION OF THE EXEMPLARY EMBODIMENTS

Figure 1:
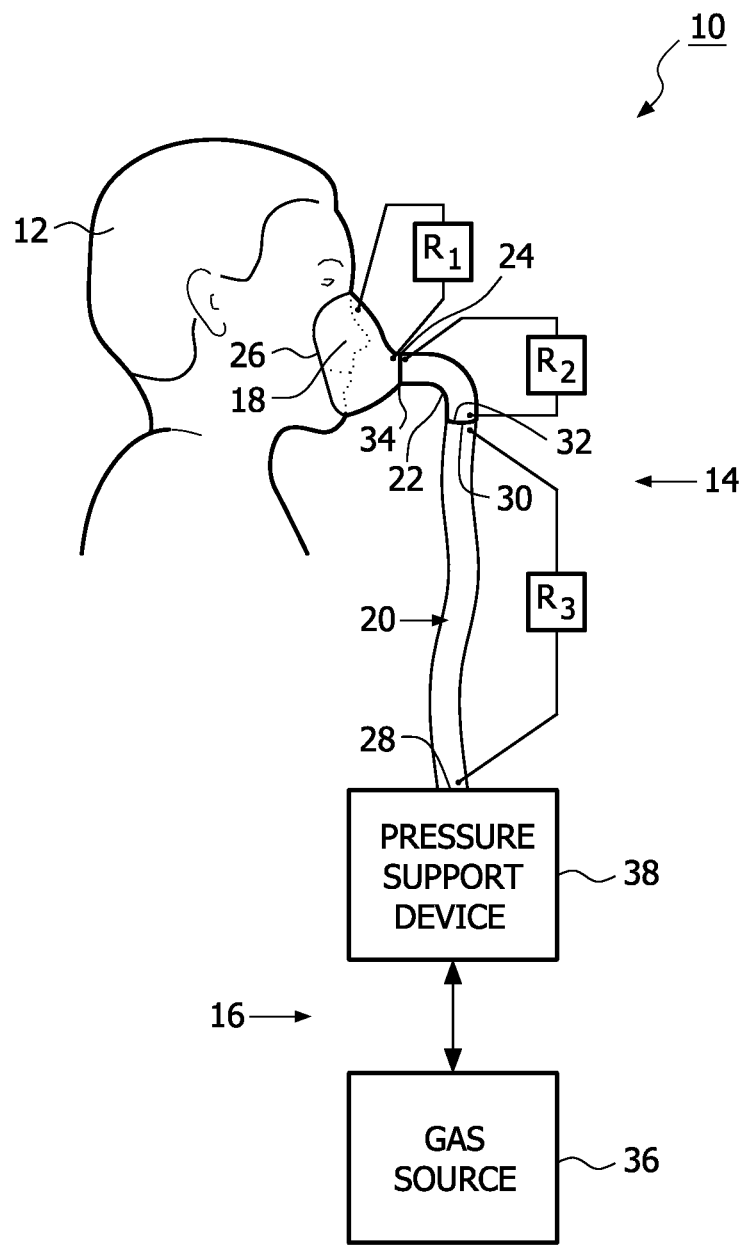
FIG. 1 illustrates a system 10 configured to deliver a pressurized flow of gas to the airway of a subject, in accordance with one or more embodiments of the invention.

FIG. 1 illustrates a system 10 configured to deliver a pressurized flow of gas to the airway of a subject 12 for therapeutic purposes. For example, system 10 may deliver the pressurized flow of gas to the airway of the subject as part of a Positive Airway Pressure ("PAP") treatment, as part of a ventilation therapy, and/or for other therapeutic purposes. In one embodiment, system 10 includes one or more of a circuit 14 and a pressure generator 16.

Circuit 14 defines a gas flow path between pressure generator 16 and the airway of subject 12. As such, circuit 14 is configured to deliver the pressurized flow of gas from pressure generator 16 to the airway of subject 12. In one embodiment, circuit 14 includes one or more of an interface appliance 18, a conduit 20, and a connecting module 22.

Interface appliance 18 is configured to provide gas to and receive gas from the airway of subject 12. Interface appliance 18 forms a flow path between a conduit interface opening 24 and one or more subject interface openings 26 (e.g., one as shown in FIG. 1, two in the case of a nasal cannula, etc.). Conduit interface opening 24 communicates gas between the interior of interface appliance 18 and the rest of circuit 14, and subject interface opening 26 communicates gas between the airway of subject 12 and the interior of interface appliance 18. Interface appliance 18 may include may include either an invasive or non-invasive appliance for communicating gas between circuit 14 and the airway of subject 12. For example, interface appliance 18 may include a nasal mask, nasal/oral mask, total face mask, nasal cannula, endotracheal tube, LMA, tracheal tube, and/or other interface appliance.

The flow path formed between conduit interface opening 24 and subject interface opening 26 has a resistance to gas flow referred to herein as the first resistance, and represented in FIG. 1 as $R_1$. The resistance to gas flow of a flow path may be quantified in terms of the pressure drop across the flow path. As will be appreciated, the resistance of a particular embodiment of interface appliance 18 will be a function of the physical properties of interface appliance 18. For example, the resistance of a particular embodiment of interface appliance 18 may depend on one or more of the number of subject interface openings 26, the size of subject interface openings 26 and conduit interface opening 24, the shape of the flow path formed by interface appliance 18, the distance between conduit interface opening 24 and subject interface opening(s) 26, and/or other physical properties of the particular embodiment of interface appliance 18.

Conduit 20 forms a flow path between a first opening 28 and a second opening 30. First opening 28 receives gas from pressure generator 16. Gas within the flow path formed by conduit 20 is communicated to conduit interface opening 24 via second opening 30. In one embodiment, conduit 20 is flexible. The flow path formed between first opening 28 and second opening 30 has a resistance to gas flow referred to herein as the second resistance, and represented in FIG. 1 as $R_2$. The second resistance is a function of the physical properties of conduit 20. For example, the second resistance may be a function of one or more of the length of the flow path formed by conduit 20, the cross-sectional shape and/or area of conduit 20, the smoothness of the walls of conduit 20, and/or other physical properties of conduit 20.

Connection module 22 is configured to connect the flow path formed by conduit 20 with the flow path formed by interface appliance 18. As such, connection module 22 forms a flow path between a first opening 32 and a second opening 34. Generally, to enhance the comfort of using interface appliance 18, connection module 22 may include an elbow bend and/or swivel that causes the flow path formed by connection module 22 to bend and/or swivel during use. In one embodiment, connection module 22 includes one or more exhaust openings or valves that operate to exhaust gas exhaled by subject 12 into circuit 14 (e.g., to atmosphere). It should be appreciated that in one embodiment, circuit 14 does not include a connection module. In this embodiment, conduit 20 may connect directly to interface appliance 18.

The flow path formed between first opening 32 and second opening 34 has a resistance to gas flow referred to herein as the third resistance, and represented in FIG. 1 as $R_3$. The resistance of a particular embodiment of connection module 22 will be a function of the physical properties of interface connection module 22. For example, the resistance of a particular embodiment of conduit module 22 may depend on one or more of the number of exhaust openings, the position of any exhaust openings, the shape of the flow path formed by conduit module 22, the cross-sectional shape and/or size of conduit module 22, the length of the flow path formed by conduit module 22, and/or other physical properties of the particular embodiment of interface appliance 18.

Resistance to gas flow is an additive property. As such, the overall resistance to gas flow of circuit 14 shown in FIG. 1 can be determined from an aggregation of the resistances of the individual components. For example, for the embodiment shown in FIG. 1, the overall resistance to gas flow of circuit 14 may be determined as the sum of the first resistance, the second resistance, and the third resistance.

Although circuit 14 shown in FIG. 1 is a single-limbed circuit, this is not intended to be limiting. The principles discussed herein would be practicable with a double-limbed circuit (with one branch being configured to exhaust exhaled gas) to one skilled in the art.

Pressure generator 16 is configured to generate a pressurized flow of breathable gas for delivery to the airway of subject 12 by circuit 14. One or more parameters of the pressurized flow of breathable gas generated by pressure generator 16 may be controlled by pressure generator 16 for therapeutic purposes. For example, pressure generator may control one or more of the pressure, the flow rate, the composition, and/or other parameters of the pressurized flow of breathable gas. In one embodiment, pressure generator 16 includes a gas source 36 and a pressure support device 38.

Gas source 36 includes a body or bodies of gas from which pressure support device 38 generates the pressurized flow of breathable gas that is delivered to subject 12. Gas source 36 may include any supply of breathing gas, such as, for example, ambient atmosphere, a tank of pressurized gas, a wall gas source, and/or other bodies of breathable gas. The breathing gas from gas source 36 can be any breathable gas, such as air, oxygen, an oxygen mixture, a mixture of a breathing gas and a medication, which can be in gaseous form (e.g., nitric oxide, nebulized, etc.), and/or other breathable gases.

Pressure support device 38 includes one or more mechanisms for controlling one or more parameters of the flow of breathable gas released from pressure support device 38 to circuit 14. For example, pressure support device 38 may include one or more of a valve, a blower, a piston, a bellows, and/or other mechanisms for controlling one or more parameters of the flow of breathable gas.

In one embodiment, pressure support device 38 controls one or more of the parameters of the pressurized flow of breathable gas in accordance with a predetermined algorithm that provides a therapeutic benefit to subject 12. By way of non-limiting example, pressure support device 38 may control one or more of the pressure and/or flow rate of the breathable gas to facilitate respiration, support the airway of subject 12, to adjust the composition of gas breathed by subject 12, and/or for other therapeutic purposes.

Figure 2:
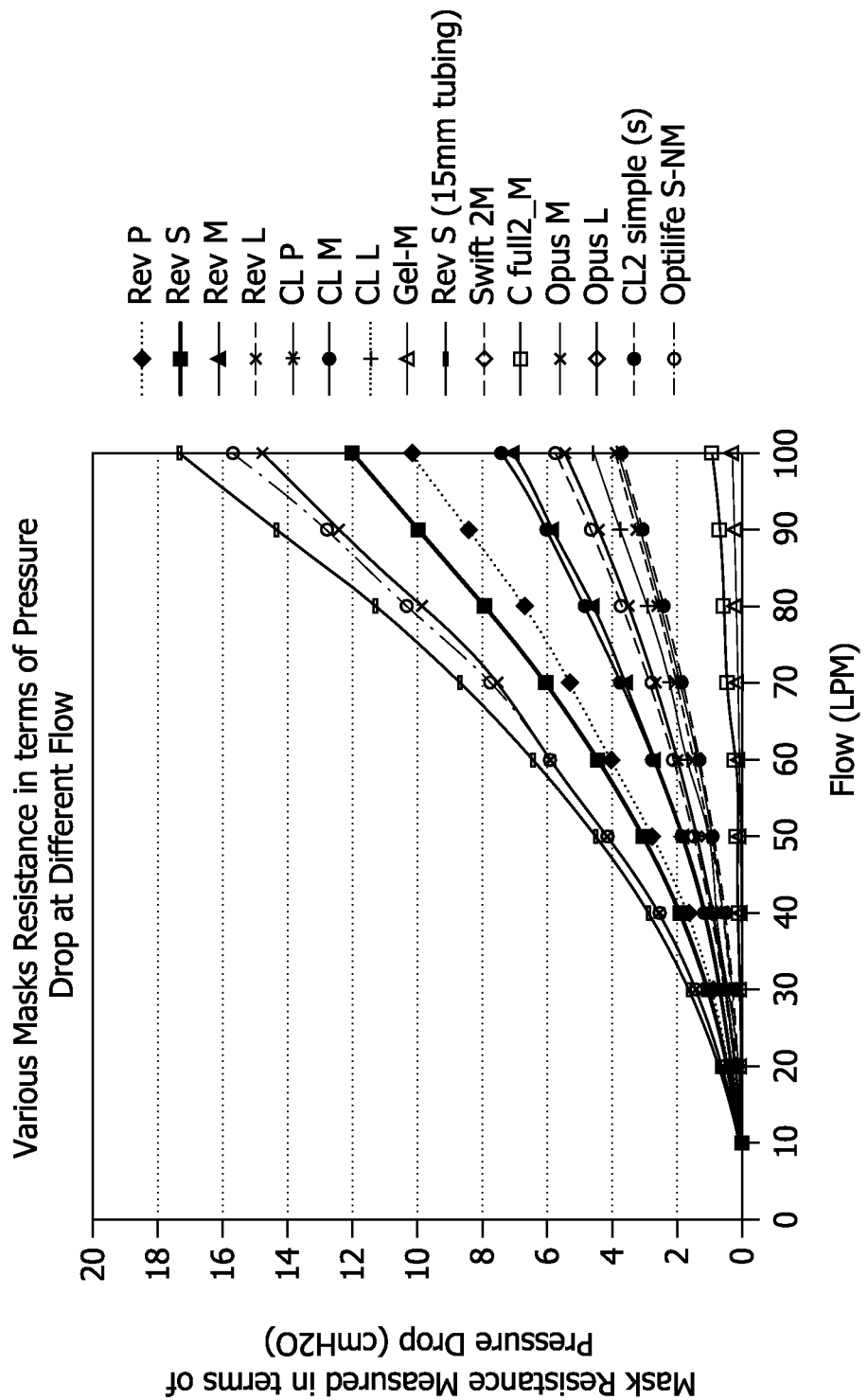
FIG. 2 is a plot of flow vs. resistance for a plurality of different interface appliances.

As was mentioned above, resistance to gas flow within circuit 14 will cause a pressure drop between first opening 28 of conduit 20, where gas is introduced to circuit 14, and patient interface opening 26 of patient interface appliance 18, where gas is communicated between circuit 14 and subject 12. This pressure drop is a function of flow. By way of illustration, FIG. 2 is a plot of flow versus pressure drop in circuits including interface appliances with different resistances. The appliances with higher resistances (e.g., nasal cannula systems, nare pillow interfaces, etc.) are represented by the plots that indicate relatively high pressure drops across the circuit at the higher flows, and appliances with lower resistances (e.g., oral-nasal masks, etc.) are represented by the plots that indicate relatively low pressure drops across the circuit at higher flows. As a frame of reference, pressure support devices generate about 120 LPM of flow at 20 $cmH_2O$ of pressure. As can be seen in FIG. 2, the loss of pressure within the circuit at typical operating levels is not trivial. Further, the relative differences in the losses caused by differently configured circuits is also significant.

Figure 3:
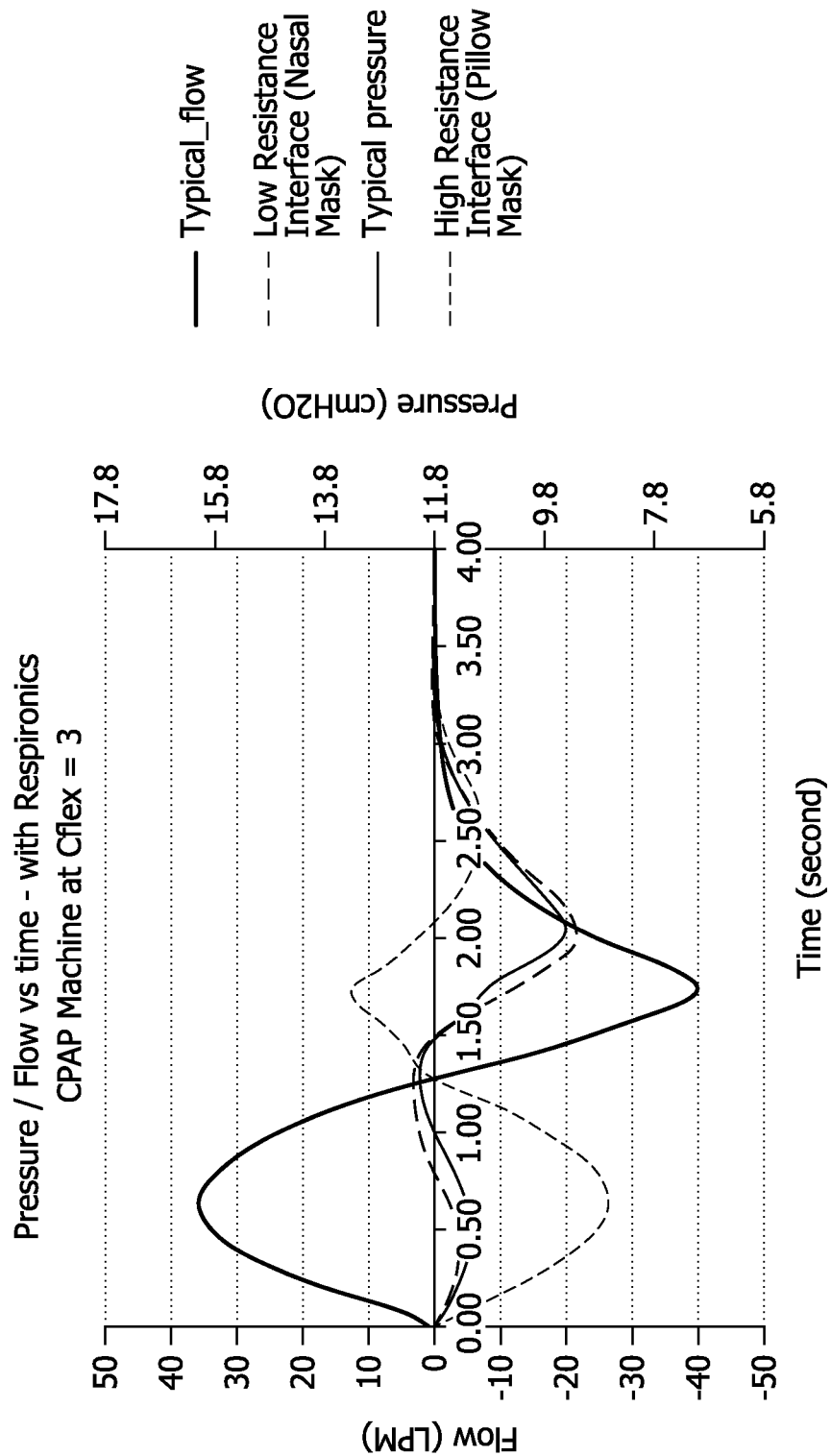
FIG. 3 is a plot of flow and pressure vs. time as a pressurized flow of breathable gas is delivered to a subject, in accordance with one or more embodiments of the invention.

FIG. 3 is a plot that shows flow vs. time for a single breathing cycle for a flow of pressurized gas generated by a pressure generator in accordance with a therapeutic algorithm that dictates the pressure and flow of the gas as the gas leaves the pressure generator. On the same axis, the pressure vs. time at an interface appliance delivering the pressurized flow of gas to the airway of a subject is shown for three separate circuit configurations. The three circuit configurations include a high resistance configuration, a low resistance configuration, and a medium resistance configuration. As can be seen in FIG. 3, the relative resistance level of the circuit can significantly impact the pressure levels experienced by the subject if relative circuit resistance is not accounted for in generating the pressurized flow of breathable gas.

Generally, the overall resistance of a circuit is a function of the individual resistances of the components forming the circuit (e.g., the interface appliance, the conduit, the connecting module, etc.). Typically, these components are interchangeable to enable the subject to configure a circuit that is suited to his liking. For example, the subject may include a conduit that is longer or shorter, the subject may include a mask or a nasal cannula as the interface appliance based on personal preference, and/or may otherwise configure circuit 14 with components based on personal preference.

Some conventional systems disregard the variability of circuit resistance caused by circuit customization. These systems assume resistance to be some predetermined value even though this assumption is likely not valid and, to some extent, may impact the delivery of the pressurized flow of breathable gas to the subject (e.g., as is demonstrated in FIGS. 2 and 3). In other conventional systems, to account for variation in overall circuit resistant caused by the componentry selected by the subject for inclusion in the circuit, measurements of the overall resistance may be made, and then the parameters of the pressurized flow of breathable gas generated by the pressure generator are adjusted based on the measured resistance. However, accounting for circuit resistance in this manner causes the control of the pressure generator to be relatively complicated, and may be susceptible to inaccuracies in the measurement of circuit resistance.

Figure 4:
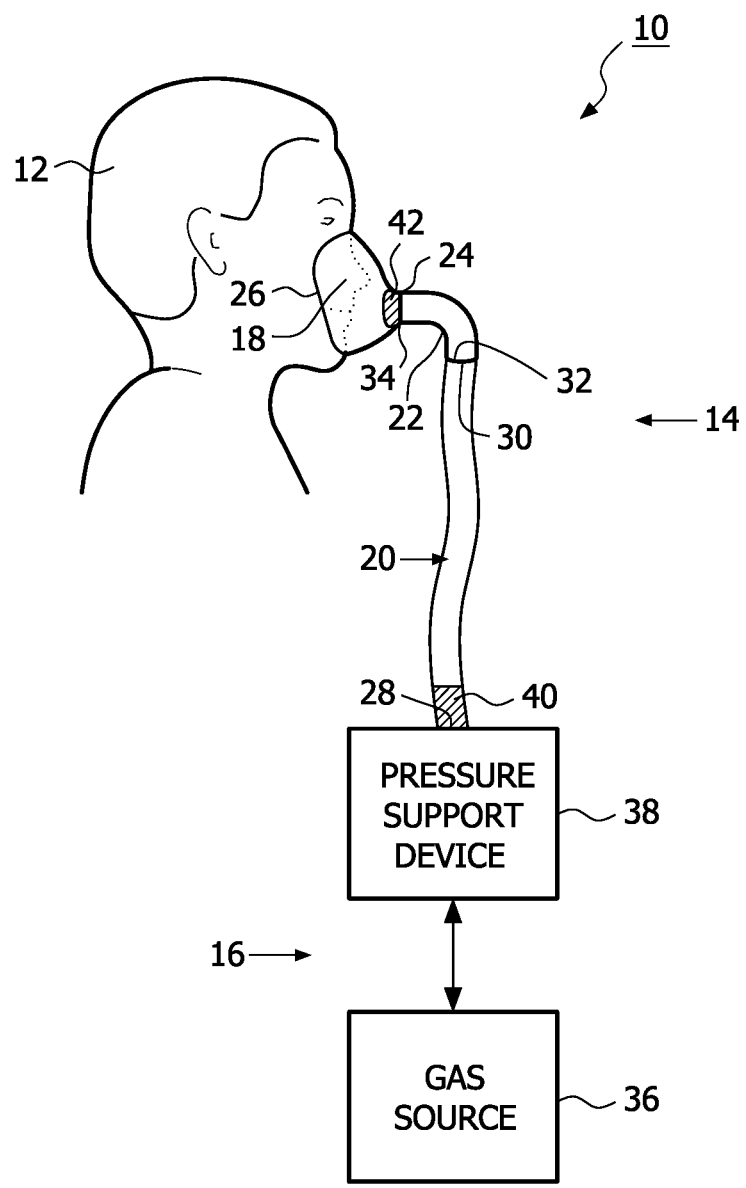
FIG. 4 illustrates a system 10 configured to deliver a pressurized flow of gas to the airway of a subject, in accordance with one or more embodiments of the invention.

FIG. 4 illustrates an embodiment of system 10 in which circuit resistance is accounted for without making adjustments to the parameters of the pressurized flow of breathable gas generated by pressure support device 38 that are specific to the components used to form circuit 14. In this embodiment, rather than adjusting the parameters of the pressurized flow of breathable gas as the gas leaves pressure support device 38 to account for a specific circuit configuration, the overall resistance of circuit 14 is elevated to a predetermined level.

The overall resistance of circuit 14 is elevated to a predetermined level by the inclusion in circuit 14 of one or more flow limiting features. The one or more flow limiting features are features are provided within circuit 14 for the purpose of supplementing the overall circuit resistance. By way of non-limiting example, the one or more flow limiting features may include one or more of an extended length, an increased or decreased diameter, an irregular cross-section, a surface finish, a turn or elbow, corrugations, a lumen hose with pressure pick-off in-lining, increased or decreased exhaust purging, and/or other features.

In one embodiment, at least one of the one or more flow limiting features is provided integrally with one or more of the previously discussed components of circuit 14. For example, in FIG. 4, conduit 20 is depicted including a section 40 having one or more flow limiting features therein to supplement the resistance of circuit 14. The amount of supplemental resistance provided by the one or more flow limiting features included in section 40 of conduit 20 may be determined at the time of manufacture based on other physical properties of conduit 20. For instance, if conduit 20 is relatively short and/or has a relatively large cross-sectional area, the one or more flow limiting features included in section 40 of conduit 20 are formed to have a relatively large supplemental resistance.

Similarly, if conduit 20 is relatively long and/or has a relatively small cross-sectional area, the one or more flow limiting features included in section 40 of conduit 20 are formed to have a relatively small supplemental resistance. In this manner, a set of conduits having different physical properties (e.g., different length, flexibility, cross-section, etc.) can be manufactured to have a common resistance (e.g., the conventional circuit resistance plus the supplemental resistance provided by section 40). Thus, no matter which of the set of conduits subject 12 selects for inclusion in circuit 14, the overall resistance of circuit 14 will not be impacted.

As another example of one or more flow limiting features provided integrally with one or more of the previously discussed components of circuit 14, in FIG. 4, interface appliance 18 is depicted as including a section 42 in which one or more flow limiting features are formed so as to supplement the overall resistance of circuit 14. The amount of supplemental resistance to include in section 42 of interface appliance 18 by virtue of the one or more flow-limiting structures is determined at the time of manufacture based on other physical properties of interface appliance 18 that impact resistance. If the physical properties of interface appliance 18 cause the resistance of interface appliance 18 to be relatively low (e.g., for a oral-nasal mask), then the one or more flow limiting features included in section 42 of interface appliance 18 are formed to have a relatively large supplemental resistance.

Similarly, if the physical properties of interface appliance 18 cause the resistance of interface appliance 18 to relatively high (e.g., for a nasal cannula), the one or more flow limiting features included in section 42 of interface appliance 18 are formed to have a relatively small supplemental resistance. Thus, for a circuit including any of a variety of different types of interface appliances, resistance for the circuit will still be the same (e.g., the conventional circuit resistance plus the supplemental resistance provided by section 42).

It should be appreciated that sections 40 and 42 are not the only sections of circuit 14 in which flow limiting features may be disposed to supplement the resistance of circuit 14. Instead, these two sections are provided only as examples. One skilled in the art will recognize a plurality of other sections of circuit 14 in which flow limiting features may be disposed to supplement the resistance circuit 14 to a predetermined level to facilitate the delivery of the pressurized flow of gas generated by pressure support device 38 to the airway of subject 12 with levels at or near the airway of subject 12 that are dictated by a predetermined algorithm.

Figure 5:
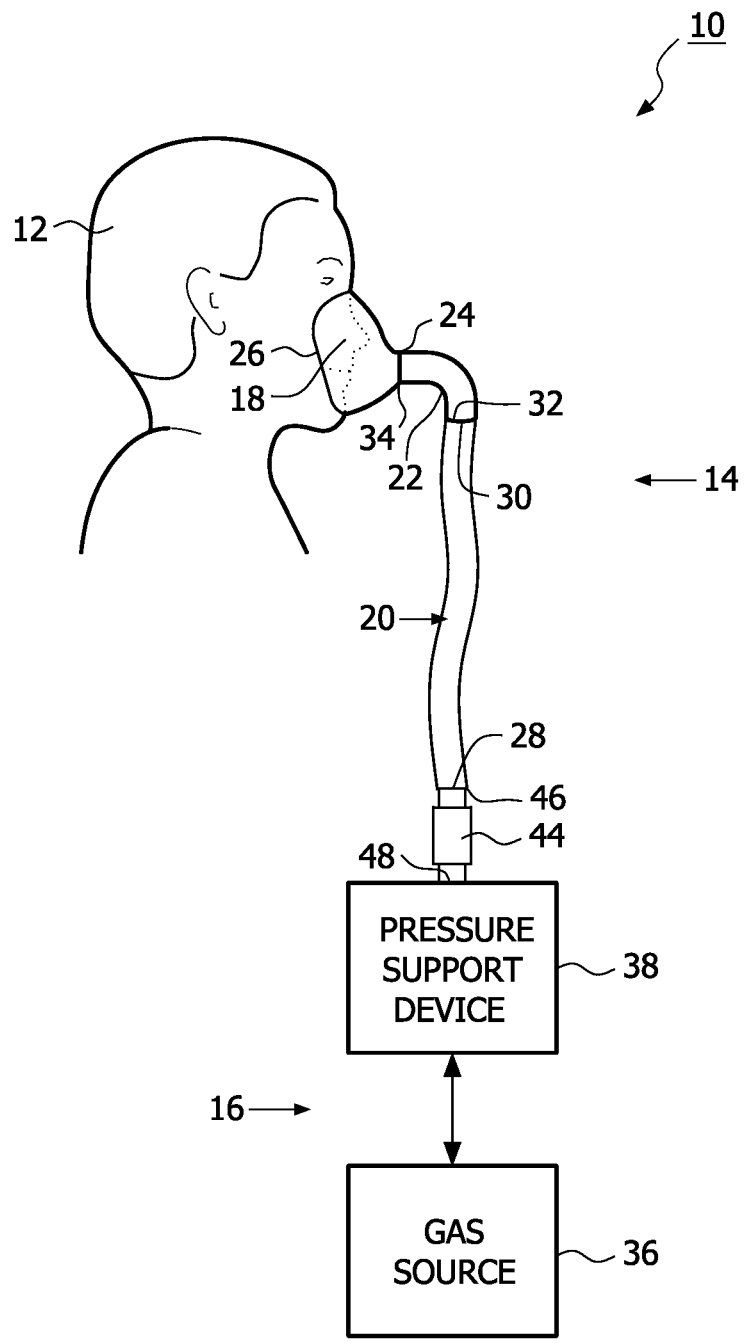
FIG. 5 illustrates a system 10 configured to deliver a pressurized flow of gas to the airway of a subject, in accordance with one or more embodiments of the invention.

FIG. 5 illustrates an embodiment of system 10 in which the impact of overall circuit resistance on parameters of the pressurized flow of breathable gas generated by pressure support device 38 is accounted for without making adjustments to the generation of the pressurized flow of breathable gas that are specific to the components used to form circuit 14. In the embodiment shown in FIG. 5, the overall resistance of circuit 14 is supplemented to a predetermined level regardless of the individual components used to form circuit 14. In particular, the overall resistance of circuit 14 is elevated to a predetermined level by selectably inserting one or more resistance modules 44, each having a supplemental resistance associated therewith, into circuit 14.

A given resistance module 44 forms a flow path between a first opening 46 and a second opening 48. One or more flow limiting features are disposed in the flow path formed by resistance module 44 between first opening 46 and second opening 48. The one or more flow limiting features may include one or more of an extended length, an increased or decreased diameter, an irregular cross-section, a surface finish, a turn or elbow, corrugations, and/or other features.

In one embodiment, individual resistance modules 44 have different supplemental resistances associated therewith, and subject 12 inserts the resistance module(s) 44 into circuit 14 that correspond to other components selected by subject 12 for inclusion within circuit 14. For example, if subject 12 includes a interface appliance 18 within circuit 14 with a relatively small resistance (e.g., an oral-nasal mask), subject 12 may insert one of resistance modules 44 into circuit 14 (or an appropriate combination of two or more resistance modules 44) that has a relatively large supplemental resistance, thereby ensuring that the overall resistance of circuit 14 will reach a predetermined level. As another example, if subject 12 includes a interface appliance 18 within circuit 14 with a relatively large resistance (e.g., a nasal cannula), subject 12 may insert one of resistance modules 44 into circuit 14 that has a relatively small supplemental resistance to provide circuit 14 with the predetermined level of overall resistance.

In one embodiment, resistance modules 44 are provided to subject 12 with a description of the types of circuit componentry with which they should be used. For instance, a resistance module 44 having a relatively high supplemental resistance may be provided to subject 12 with instructions and/or indicia that indicates that this resistance module 44 should be included in a circuit with a mask that includes an oral-nasal mask system. Similarly, a resistance module 44 having a somewhat lower supplemental resistance may be provided to subject 12 with instructions and/or indicia indicating that this resistance module 44 should be included in a circuit with a mask that includes a nasal mask system (which would have a resistance lower than an oral-nasal mask system and higher than a nasal cannula). By following the instructions and/or indicia accompanying the provided resistance modules 22, subject 12 will be able to configure a circuit having an overall resistance that is at or near the predetermined level of resistance. In turn, this will facilitate the provision of the pressurized flow of gas to subject 12 according to the appropriate treatment algorithm with an enhanced precision.

In one embodiment, resistance module 44 may be inserted in circuit 14 between pressure generator 16 and conduit 20 (e.g., with first opening 46 of resistance module 44 releasably engaged with first opening 28 of conduit 20). However, this should not be seen as being limiting. In one embodiment, one or more resistance modules 44 may be selectably inserted within circuit 14 between conduit 20 and connecting module 22, between connecting module 22 and interface appliance 18, between conduit 20 and interface appliance 18 (if the embodiment does not include connecting module 22), and/or at other points within circuit 14.

Figure 6:
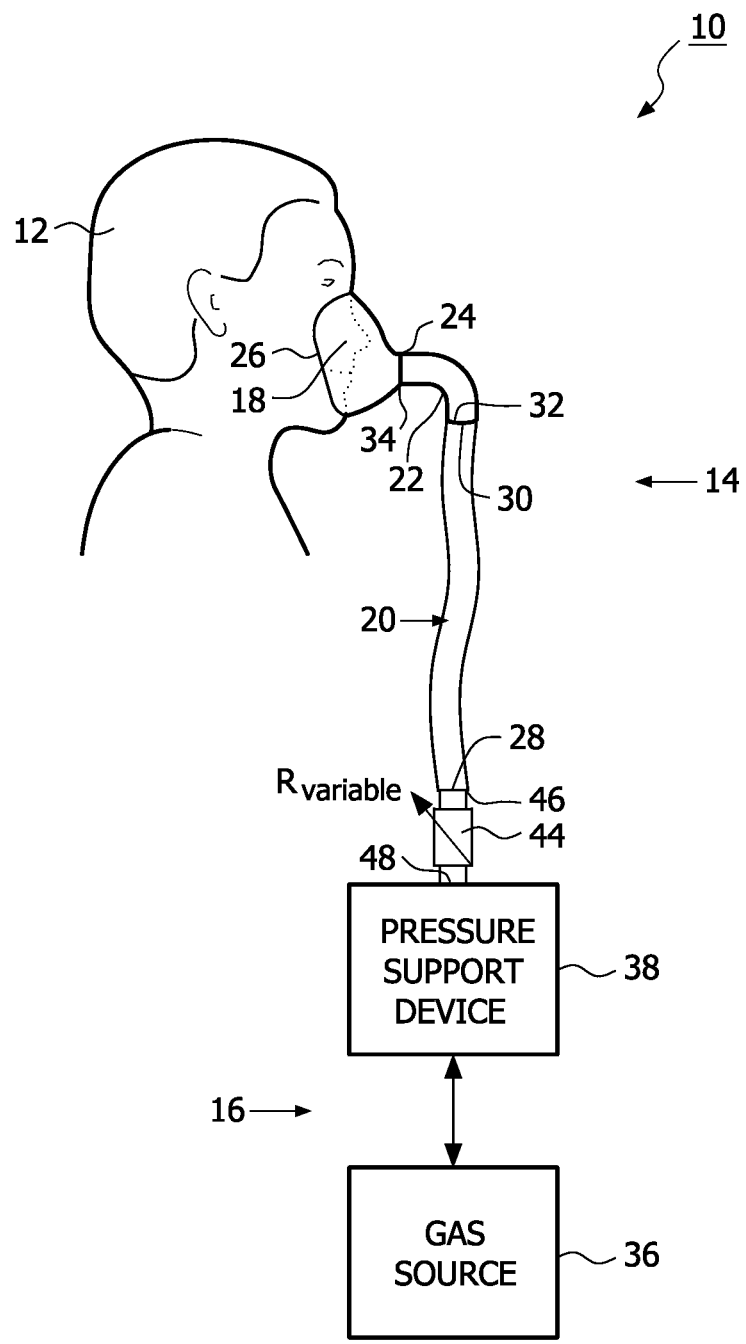
FIG. 6 illustrates a system 10 configured to deliver a pressurized flow of gas to the airway of a subject, in accordance with one or more embodiments of the invention.

FIG. 6 illustrates an embodiment of system 10 in which the impact of overall circuit resistance on parameters of the pressurized flow of breathable gas generated by pressure support device 38 is accounted for without making adjustments to the generation of the pressurized flow of breathable gas that are specific to the components used to form circuit 14. In the embodiment shown in FIG. 6, the overall resistance of circuit 14 is supplemented to a predetermined level by a resistance module 44 having an adjustable supplemental resistance. The supplemental resistance is made adjustable by providing one or more flow limiting features that can be manipulated to provide more or less resistance within the flow path of resistance module 44. For example, the one or more flow limiting features may include a valve with an adjustable valve opening size, a movable piston, a bend, and/or other flow limiting features. The supplemental resistance of resistance module 44 may be adjustable automatically and/or manually.

In one embodiment, the supplemental resistance of resistance module 44 is adjusted automatically based on one or more parameters of the gas within circuit 14. In this embodiment, one or more sensors (not shown) monitor one or more parameters of the gas within circuit 14 (e.g., flow rate, pressure, etc.). Information generated by the one or more sensors is used to manipulate the one or more flow limiting features within the flow path of resistance module 44 such that the supplemental resistance of resistance module 44 is adjusted to bring the overall resistance of circuit 14 to (or near) a predetermined resistance level. The processing functionality required to determine the appropriate manipulation of the flow limiting features and/or to control the automatic manipulation of the flow limiting features may be provided by a processor (not shown) that is part of pressure support device 38 or a processor that is external and separate from pressure support device 38.

Figure 7:
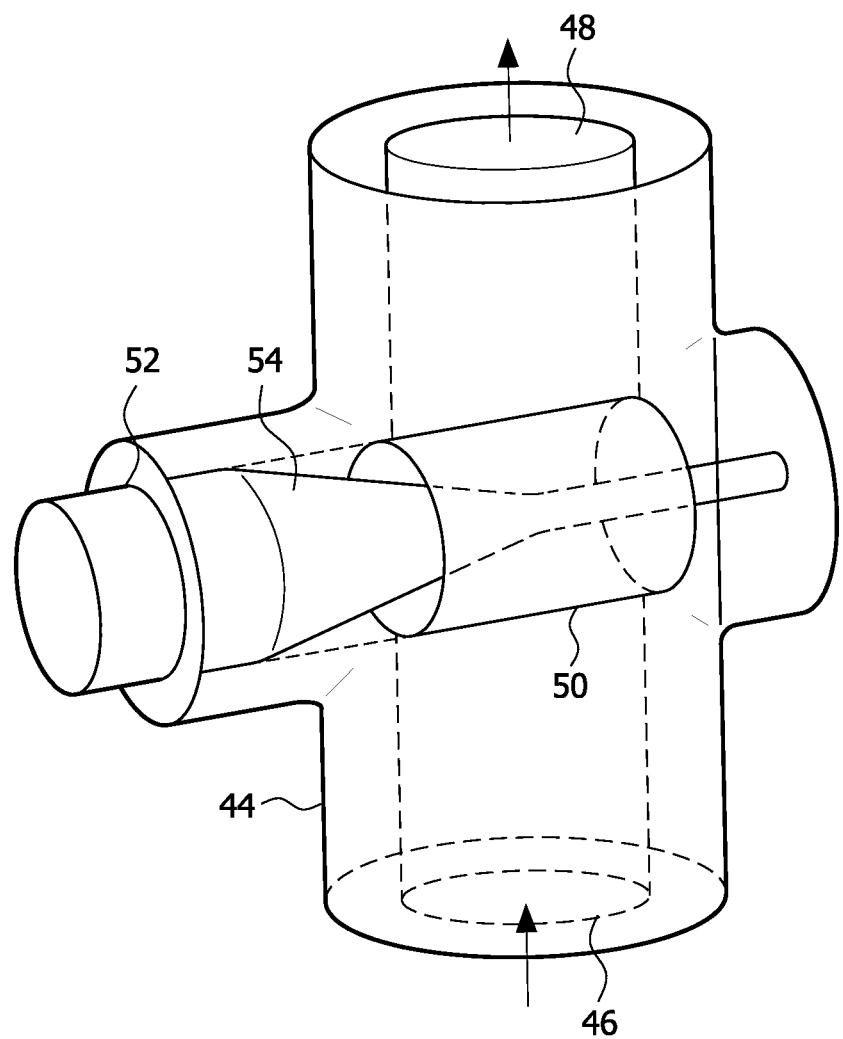
FIG. 7 illustrates a resistance module having a variable resistance to the flow of gas, according to one or more embodiments of the invention.

In one embodiment, the supplemental resistance of resistance module 44 is adjusted automatically in a more passive manner. By way of illustration, FIG. 7 illustrates an embodiment of resistance module 44 in which the pressure within circuit 14 is implemented to manipulate the one or more flow limiting features of resistance module 44. In the embodiment shown in FIG. 7, resistance module 44 forms a piston chamber 50 that communicates with the flow path between first opening 46 and second opening 48 and a chamber opening 52 formed on a surface of resistance module 44 away from first opening 46 and second opening 48. Resistance module 44 further includes a piston 54 that is slidably disposed within chamber 52. The cross-section of piston 54 is tapered at an end of piston 54 disposed within chamber 50. Piston 54 is biased (e.g., via spring-loading) down into chamber 50. By virtue of this bias and the tapering of piston 54, the position of piston 54 changes as the pressure within circuit 14 fluctuates. More specifically, as the pressure within circuit 14 increases piston 54 is driven out of chamber 50, thereby decreasing the supplemental resistance of resistance module 44. Similarly, as the pressure within circuit 14 decreases piston 54 moves further into chamber 50, which increases the supplemental resistance of resistance module 44.

If an interface appliance (e.g., interface appliance 18 in FIG. 1) connected to circuit 14 has a relatively high resistance (e.g., a nasal cannula), then the pressure within circuit 14 will be relatively high (due to the high resistance of the interface appliance). By contrast, if an interface appliance connected to circuit 14 has a relatively low resistance (e.g., an oral-nasal mask), the pressure within circuit 14 will be relatively low (due to the low resistance of the interface appliance). Thus, for the interface appliance with the high resistance, the pressure within circuit 14 will drive piston 54 of resistance module 44 further out of chamber 50 than the pressure within circuit 14 if the interface applicant has a low resistance. This causes the supplemental resistance of resistance module 44 to be greater for instances in which the resistance of the interface appliance is relatively low and less for instances in which the resistance of the interface appliance is relatively high, thereby supplementing the overall resistance of circuit 14 to maintain the overall level of resistance at or near a predetermined level regardless of the relative resistance of the interface appliance (and/or other components in circuit 14).

Returning to FIG. 6, in one embodiment, the supplemental resistance of resistance module 44 is manually adjustable. In this embodiment, resistance module 44 includes a control (not shown) that is manually engagable by subject 12 to manipulate the one or more flow limiting features in resistance module 44. The control may include a plurality of control settings that each correspond to different levels of supplemental resistance. In some instances, the control is indexed to the plurality of control settings. In order to facilitate proper adjustment of the supplemental resistance by subject 12, in one embodiment, subject 12 is provided with instructions and/or indicia that inform subject 12 which of the control settings resistance module 44 should be set to based on components that have been selected for insertion in circuit 14.

Figure 8:
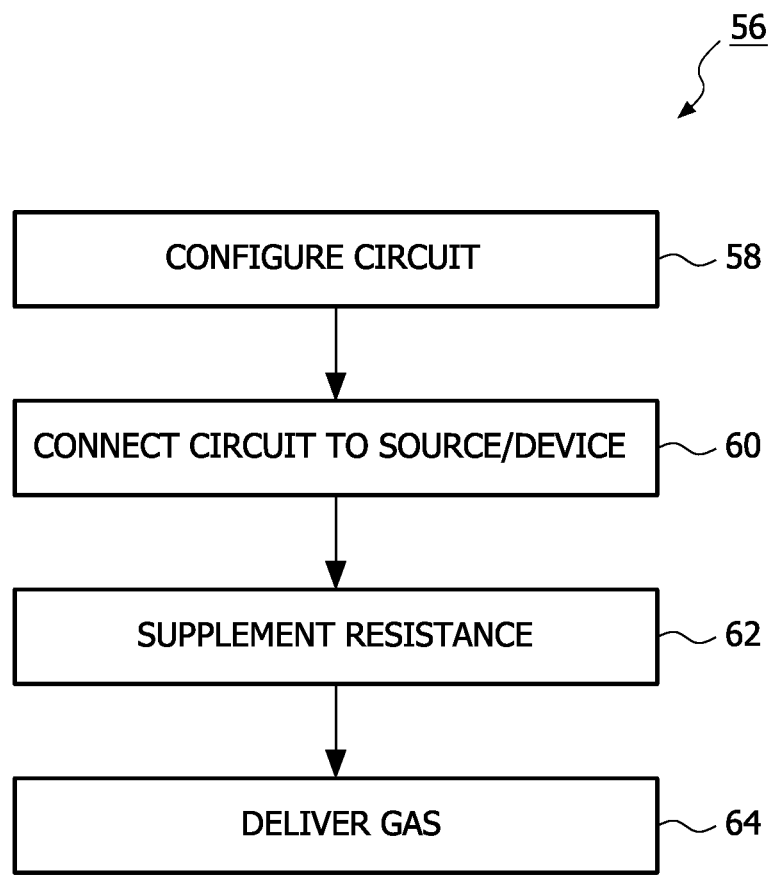
FIG. 8 is a flow chart illustrating a method of providing a circuit that defines a flow path between a pressure generator and an airway of a subject, in accordance with one or more embodiments of the invention.

FIG. 8 illustrates a method 56 of providing a circuit that defines a flow path between a pressure generator and an airway of a subject to enable the provision of gas from the pressure generator to the airway of the subject. The operations of method 56 presented below are intended to be illustrative. In some embodiments, method 56 may be accomplished with one or more additional operations not described, and/or without one or more of the operations discussed. Additionally, the order in which the operations of method 20 are illustrated in FIG. 8 and described below is not intended to be limiting.

At an operation 58, a circuit is configured that forms a flow path for delivering gas from a pressure generator to the airway of a subject. The circuit may include one or more of a conduit, an interface appliance, and/or a connection module. In one embodiment, the circuit is similar to or the same as circuit 14 (shown in FIGS. 1 and 4-6, and described above).

At an operation 60, the circuit is connected to a pressure generator configured to generate a pressurized flow of breathable gas. The pressure generator may include one or both of a gas source and/or a pressure support device. In one embodiment, the pressure generator is the same as or similar to pressure generator 16 (shown in FIGS. 1 and 4-6, and described above).

At an operation 62, the overall resistance of the circuit is supplemented so that the overall resistance of the circuit to gas flow reaches a predetermined resistance. The predetermined resistance may be a level of resistance that the pressure generator accounts for in generating the pressurized flow of breathable gas. In some instances, operation 62 includes disposing one or more flow limiting features within the flow path formed by the circuit. The one or more flow limiting features may be formed integrally with the circuit, or may be selectively inserted into the circuit. In one embodiment, operation 62 includes selectively inserting a resistance module into the circuit that is the same as or similar to resistance module 44 (shown in FIGS. 4-7, and described above).

At an operation 64, the pressurized flow of breathable gas generated by the pressure generator is delivered to the subject through the circuit.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A system configured to deliver a pressurized flow of gas to an airway of a subject, comprising:
a pressure generator configured to generate the pressurized flow of gas and control one or more parameters of the pressurized flow of gas using a predetermined algorithm based on and accounting for a predetermined circuit resistance level; and a circuit selectively configurable by the subject that defines a gas flow path between the pressure generator and the airway of the subject, wherein the circuit, when selectively configured by the subject, includes:

an interface appliance configured to provide gas to and receive gas from the airway of the subject, the interface appliance forming a flow path between a conduit interface opening and one or more subject interface openings, wherein the one or more subject interface openings communicate gas between the airway of the subject and the interior of the interface appliance, and wherein the flow path formed by the interface appliance between the conduit interface opening and the one or more subject interface openings has a first resistance to gas flow;

a conduit that forms a flow path between a first opening and a second opening, wherein the first opening receives gas from the pressure generator, wherein gas with the flow path formed by the conduit is communicated to the conduit interface opening of the interface appliance via the second opening, and wherein the flow path formed by the conduit between the first opening and the second opening has a second resistance to gas flow; and one or more flow limiting features disposed within the circuit, the one or more flow limiting features structured to provide a predetermined supplemental resistance to gas flow within the circuit, and wherein the overall resistance to gas flow within the circuit is a function, at least in part, of an aggregation of the first resistance, the second resistance, and the predetermined supplemental resistance, and wherein the predetermined supplemental resistance is chosen such that the predetermined supplemental resistance increases the overall resistance to gas flow within the circuit to the predetermined circuit resistance level when the circuit is selectively configured to include the interface appliance and the conduit.

2. The system of claim 1, wherein the one or more flow limiting features comprise at least one flow limiting feature formed integrally on the interface appliance.

3. The system of claim 2, wherein the at least one flow limiting feature formed integrally on the interface appliance comprises a restriction on gas flow formed at or near the conduit interface opening.

4. The system of claim 1, further comprising a removable resistance module indicated as corresponding to the interface appliance and the conduit and forming a flow path between a first module opening and a second module opening, the removable resistance module having at least one of the one or more flow limiting features disposed in the flow path between the first module opening and the second module opening, wherein removable resistance module is selectably insertable into the circuit to increase the overall resistance to gas flow within the circuit to the predetermined circuit resistance level when the circuit is selectively configured to include the interface appliance and the conduit.

5. The system of claim 4, wherein the removable resistance module is selectably insertable into the circuit by releasably engaging the first module opening with the first opening of the conduit or the conduit interface opening of the interface appliance.

6. The system of claim 5, wherein the removable resistance module is further selectably insertable into the circuit by releasably engaging the second module opening with the second opening of the conduit.

7. The system of claim 4, further comprising a connection module that connects the flow path formed by the conduit with the flow path formed by the interface appliance, the connection module forming one or more exhaust openings configured to exhaust gas exhaled by the subject from the circuit, wherein the connection module has a third resistance to gas flow, and wherein the overall resistance to gas flow within the circuit is a function, at least in part, of an aggregation of the first resistance, the second resistance, the third resistance, and the predetermined supplemental resistance.

8. The system of claim 7, wherein the removable resistance module is selectably insertable into the circuit by releasably engaging the first module opening with the connection module.

9. The system of claim 1, further comprising a plurality of removable resistance modules indicated as corresponding to the interface appliance and the conduit, wherein each of the removable resistance modules forms a flow path that is selectably insertable into the circuit and includes at least one of the one or more flow limiting features.

10. A method of providing a pressurized flow of gas to an airway of a subject, comprising:

configuring a circuit that forms a flow path for delivering gas from a pressure generator to the airway of the subject, the circuit comprising:

an interface appliance configured to provide gas to and receive gas from the airway of the subject, the interface appliance forming a flow path between a conduit interface opening and one or more subject interface openings, wherein the one or more subject interface openings communicate gas between the airway of the subject and the interior of the interface appliance, and wherein the flow path formed by the interface appliance between the conduit interface opening and the one or more subject interface openings has a first resistance to gas flow; and a conduit that forms a flow path between a first opening and a second opening, wherein the first opening receives gas from the pressure generator, wherein gas within the flow path formed by the conduit is communicated to the conduit interface opening of the interface appliance via the second opening, and wherein the flow path formed by the conduit between the first opening and the second opening has a second resistance to gas flow;

supplementing the overall resistance of the circuit to gas flow so that the overall resistance of the circuit to gas flow reaches a predetermined circuit resistance, wherein supplementing the overall resistance of the circuit comprises including within the circuit one or more flow limiting features, the one or more flow limiting features providing a predetermined supplemental resistance to gas flow within the circuit that increases the overall resistance of the circuit to the predetermined circuit resistance;

generating the pressurized flow of gas and controlling one or more parameters of the pressurized flow of gas in the pressure generator using a predetermined algorithm based on and accounting for the predetermined circuit resistance level; and delivering the pressurized flow of gas to the subject through the circuit.

11. The method of claim 10, wherein the one or more flow limiting features comprise at least one flow limiting feature formed integrally on the interface appliance.

12. The method of claim 10, wherein including within the circuit one or more flow limiting features comprises selectably inserting a removable resistance module indicated as corresponding to the interface appliance and the conduit into the circuit, the removable resistance module forming a flow path between a first module opening and a second module opening, the removable resistance module having at least one of the one or more flow limiting features disposed in the flow path between the first module opening and the second module opening.

13. The method of claim 12, wherein the removable resistance module is selectably inserted into the circuit at least in part by releasably engaging the first module opening with the first opening of the conduit or the conduit interface opening of the interface appliance.

14. The method of claim 13, wherein the removable resistance module is further selectably inserted into the circuit at least in part by releasably engaging the second module opening with the second opening of the conduit.

15. The method of claim 12, wherein the circuit further comprises a connection module that connects the flow path formed by the conduit with the flow path formed by the interface appliance, the connection module forming one or more exhaust openings configured to exhaust gas exhaled by the subject from the circuit, the connection module having a third resistance to gas flow, and wherein the overall resistance to gas flow within the circuit is a function, at least in part, of an aggregation of the first resistance, the second resistance, the third resistance, and the predetermined supplemental resistance.

* * * * *